United States Patent [19]
Scheiner et al.

[11] Patent Number: 6,085,119
[45] Date of Patent: Jul. 4, 2000

[54] SINGLE PASS ENDOCARDIAL LEAD FOR MULTI-SITE ATRIAL PACING

[75] Inventors: Avram Scheiner, Vadnais Heights; Qingsheng Zhu, Little Canada, both of Minn.

[73] Assignee: Cardiac Pacemakers, Inc., St. Paul, Minn.

[21] Appl. No.: 09/121,019

[22] Filed: Jul. 22, 1998

[51] Int. Cl.[7] .................................................. A61N 1/05
[52] U.S. Cl. ........................ 607/122; 607/9; 600/393; 600/375
[58] Field of Search ................... 607/116, 119, 607/122, 126, 127, 128, 9, 123; 600/374, 375, 393

[56] References Cited

U.S. PATENT DOCUMENTS

| | | | |
|---|---|---|---|
| 3,614,955 | 10/1971 | Mirowski | 128/419 D |
| 3,804,098 | 4/1974 | Friedman | 128/404 |
| 3,866,615 | 2/1975 | Hewson | 607/4 |
| 3,942,536 | 3/1976 | Mirowski et al. | 128/419 D |
| 3,949,757 | 4/1976 | Sabel | 128/404 |

(List continued on next page.)

FOREIGN PATENT DOCUMENTS

| | | | |
|---|---|---|---|
| 0057877 | 8/1982 | European Pat. Off. | 607/121 |
| 0211166 | 2/1987 | European Pat. Off. | A61N 1/05 |
| 452278A2 | 4/1990 | European Pat. Off. | A61N 1/05 |
| 0452278 | 10/1991 | European Pat. Off. | A61N 1/05 |
| 0460324 | 12/1991 | European Pat. Off. | A61N 1/05 |
| 0573275 | 12/1993 | European Pat. Off. . | |
| 0612538 | 8/1994 | European Pat. Off. | A61N 1/05 |
| 0620024 | 10/1994 | European Pat. Off. . | |
| 0672431 | 9/1995 | European Pat. Off. | A61N 1/05 |
| 2588758 | 4/1987 | France | A61N 1/05 |
| 2827595 | 5/1978 | Germany . | |
| 3-168161 | 7/1991 | Japan . | |
| 4-40966 | 2/1992 | Japan . | |
| 2032278 | 6/1980 | United Kingdom | A61M 25/00 |
| 2240721 | 8/1991 | United Kingdom . | |
| 89/06148 | 7/1989 | WIPO | A61N 1/05 |
| 92/07616 | 5/1992 | WIPO . | |
| 96/15665 | 11/1994 | WIPO | A01N 1/05 |

OTHER PUBLICATIONS

Fain, et al., "A New Internal Defibrillation Lead System: Intrapericardial Placement Without Thoracotomy", *Abstracts Circulation*, 76, Suppl. IV, 1839 (Oct. 1987).

Jones, D.L., et al., "Internal Cardiac Defibrillation in Man: Pronounced Improvement with Sequential Pulse Delivery to Two Different Lead Orientations", *Circulation*, vol. 73, No. 3, pp. 484–41 (Mar. 1986).

(List continued on next page.)

*Primary Examiner*—Kennedy Schaetzle
*Attorney, Agent, or Firm*—Schwegman, Lundberg, Woessner & Kluth, P.A.

[57] ABSTRACT

A single-pass endocardial lead electrode is adapted for implantation within a single chamber of the heart. The lead includes a first electrode and a second electrode. The first and second electrodes are placed within the same chamber of the heart. In one embodiment, two electrodes are placed on a curved distal end of the lead. In another embodiment, the lead includes multiple legs, each leg carrying an electrode. The lead is attached to a pulse generator for producing pulses to the multiple sites within the heart.

35 Claims, 5 Drawing Sheets

U.S. PATENT DOCUMENTS

| | | | |
|---|---|---|---|
| 4,030,508 | 6/1977 | Thalen | 128/418 |
| 4,030,509 | 6/1977 | Heilman et al. | 124/419 D |
| 4,057,067 | 11/1977 | Lajos | 128/418 |
| 4,106,512 | 8/1978 | Bisping | 128/418 |
| 4,136,703 | 1/1979 | Wittkampf | 128/419 P |
| 4,154,247 | 5/1979 | O'Neill | 128/419 P |
| 4,217,913 | 8/1980 | Dutcher | 128/785 |
| 4,270,549 | 6/1981 | Heilman | 128/784 |
| 4,291,707 | 9/1981 | Heilman et al. | 128/784 |
| 4,311,153 | 1/1982 | Smits | 128/785 |
| 4,332,259 | 6/1982 | McCorkle, Jr. | 607/123 |
| 4,393,883 | 7/1983 | Smyth et al. | 128/785 |
| 4,402,329 | 9/1983 | Williams | 607/123 |
| 4,458,677 | 7/1984 | McCorkle, Jr. | 128/786 |
| 4,463,765 | 8/1984 | Gold | 128/785 |
| 4,497,326 | 2/1985 | Curry | 128/785 |
| 4,548,203 | 10/1985 | Tacker, Jr. et al. | 128/419 |
| 4,559,951 | 12/1985 | Dahl et al. | 128/642 |
| 4,567,900 | 2/1986 | Moore | 128/784 |
| 4,570,642 | 2/1986 | Kane et al. | 128/785 |
| 4,602,645 | 7/1986 | Barrington et al. | 128/786 |
| 4,603,705 | 8/1986 | Speicher et al. | 128/785 |
| 4,624,265 | 11/1986 | Grassi | 128/784 |
| 4,624,266 | 11/1986 | Kane | 128/785 |
| 4,627,439 | 12/1986 | Harris | 128/419 |
| 4,633,880 | 1/1987 | Osypka et al. | 128/642 |
| 4,646,755 | 3/1987 | Kane | 128/785 |
| 4,649,937 | 3/1987 | DeHaan et al. | 128/784 |
| 4,649,938 | 3/1987 | McArthur | 128/785 |
| 4,662,377 | 5/1987 | Heilman et al. | 128/419 |
| 4,664,113 | 5/1987 | Frisbie et al. | 128/344 |
| 4,693,258 | 9/1987 | Osypka et al. | 128/783 |
| 4,727,877 | 3/1988 | Kallok | 128/419 |
| 4,784,161 | 11/1988 | Skalsky et al. | 128/785 |
| 4,799,486 | 1/1989 | DuFault | 128/419 |
| 4,799,493 | 1/1989 | DuFault | 128/705 |
| 4,817,608 | 4/1989 | Shapland et al. | 128/419 |
| 4,817,634 | 4/1989 | Holleman et al. | 128/784 |
| 4,819,661 | 4/1989 | Heil, Jr. et al. | 128/786 |
| 4,819,662 | 4/1989 | Heil, Jr. et al. | 128/786 |
| 4,827,932 | 5/1989 | Ideker et al. | 128/419 D |
| 4,860,769 | 8/1989 | Fogarty et al. | 128/786 |
| 4,865,037 | 9/1989 | Chin et al. | 128/419 D |
| 4,886,074 | 12/1989 | Bisping | 128/785 |
| 4,905,691 | 3/1990 | Rydell | 606/47 |
| 4,924,881 | 5/1990 | Brewer | 128/785 |
| 4,938,231 | 7/1990 | Milijasevic et al. | 128/784 |
| 4,944,300 | 7/1990 | Saksena | 128/419 |
| 4,953,551 | 9/1990 | Mehra et al. | 128/419 |
| 4,967,766 | 11/1990 | Bradshaw | 128/785 |
| 4,971,070 | 11/1990 | Holleman et al. | 128/784 |
| 4,998,975 | 3/1991 | Cohen et al. | 128/419 D |
| 5,016,645 | 5/1991 | Williams et al. | 128/784 |
| 5,016,646 | 5/1991 | Gotthardt et al. | 128/784 |
| 5,020,544 | 6/1991 | Dahl et la. | 128/784 |
| 5,044,375 | 9/1991 | Bach, Jr. et al. | 128/786 |
| 5,050,601 | 9/1991 | Kupersmith et al. | 607/122 |
| 5,056,516 | 10/1991 | Spehr | 128/419 |
| 5,063,932 | 11/1991 | Dahl et al. | 128/639 |
| 5,076,285 | 12/1991 | Hess et al. | 128/186 |
| 5,083,562 | 1/1992 | de Coriolis et al. | 128/419 |
| 5,105,826 | 4/1992 | Smits et al. | 128/784 |
| 5,107,834 | 4/1992 | Ideker et al. | 128/419 |
| 5,111,811 | 5/1992 | Smits | 128/419 |
| 5,111,812 | 5/1992 | Swanson et al. | 128/419 D |
| 5,129,404 | 7/1992 | Spehr et al. | 128/785 |
| 5,133,353 | 7/1992 | Hauser | 128/419 |
| 5,133,365 | 7/1992 | Heil, Jr. et al. | 128/786 |
| 5,152,299 | 10/1992 | Soukop | 128/785 |
| 5,165,403 | 11/1992 | Mehra | 128/419 D |
| 5,174,289 | 12/1992 | Cohen | 607/9 |
| 5,174,303 | 12/1992 | Schroeppel | 128/786 |
| 5,203,348 | 4/1993 | Dahl et al. | 128/784 |
| 5,209,229 | 5/1993 | Gilli | 128/419 |
| 5,230,337 | 7/1993 | Dahl et al. | 607/5 |
| 5,259,394 | 11/1993 | Bens | 607/127 |
| 5,259,395 | 11/1993 | Li | 607/131 |
| 5,261,400 | 11/1993 | Bardy | 607/5 |
| 5,269,319 | 12/1993 | Schulte et al. | 128/786 |
| 5,271,417 | 12/1993 | Swanson et al. | 607/122 |
| 5,282,845 | 2/1994 | Bush et al. | 607/128 |
| 5,300,108 | 4/1994 | Rebel et al. | 607/127 |
| 5,300,110 | 4/1994 | Latterell et al. | 607/130 |
| 5,314,459 | 5/1994 | Swanson et al. | 607/122 |
| 5,324,327 | 6/1994 | Cohen | 607/122 |
| 5,342,414 | 8/1994 | Mehra | 607/127 |
| 5,344,439 | 9/1994 | Otten | 607/126 |
| 5,358,516 | 10/1994 | Myers et al. | 607/116 |
| 5,366,496 | 11/1994 | Dahl et al. | 607/132 |
| 5,374,286 | 12/1994 | Morris | 607/119 |
| 5,383,908 | 1/1995 | Sweeney et al. | 607/5 |
| 5,397,342 | 3/1995 | Heil, Jr. et al. | 607/129 |
| 5,405,373 | 4/1995 | Petersson et al. | 607/121 |
| 5,411,544 | 5/1995 | Mar et al. | 607/122 |
| 5,425,755 | 6/1995 | Doan | 607/119 |
| 5,425,756 | 6/1995 | Heil, Jr. et al. | 607/128 |
| 5,447,533 | 9/1995 | Vachon et al. | 607/120 |
| 5,447,534 | 9/1995 | Jammet | 607/127 |
| 5,456,706 | 10/1995 | Pless et al. | 607/122 |
| 5,456,708 | 10/1995 | Doan et al. | 607/127 |
| 5,476,501 | 12/1995 | Stewart et al. | 607/127 |
| 5,492,119 | 2/1996 | Abrams | 128/642 |
| 5,500,008 | 3/1996 | Fain | 607/5 |
| 5,522,874 | 6/1996 | Gates | 607/127 |
| 5,531,780 | 7/1996 | Vachon | 607/120 |
| 5,534,022 | 7/1996 | Hoffmann et al. | 607/122 |
| 5,545,205 | 8/1996 | Schulte et al. | 607/123 |
| 5,554,178 | 9/1996 | Dahl et al. | 607/122 |
| 5,578,068 | 11/1996 | Laske et al. | 607/126 |
| 5,964,795 | 10/1999 | McVenes et al. | 607/122 |

OTHER PUBLICATIONS

U.S. application No. 09/121,020, filed Jul. 22, 1998 entitled "Single pass Defibrillation/PacingLead with Passively Attached Electrode for pacing and Sensing".

U.S. application No. 09/121,018, filed Jul. 22, 1998 entitled "Single Pass Defibrillation/Pacing lead with passively Attached Electrode for pacing and Sensing".

U.S. application No. 09/121,006, filed Jul. 22, 1998 entitled "Single pass Lead Having Retractable, Actively Attached Electrode for Pacing and Sensing".

U.S. application No. 09/121,288, filed Jul. 22, 1998 entitled "High Impedance Electrode Tip".

U.S. application No. 09/120,824, filed Jul. 22, 1998 entitled "Single Pass Lead System".

U.S. application No. 09/121,005, filed Jul. 22, 1998 entitled "Single Pass Lead and System with Active and Passive Fixation Elements".

SINGLE PASS ENDOCARDIAL LEAD FOR MULTI-SITE ATRIAL PACING

FIELD OF THE INVENTION

The present invention relates to the field of leads for correcting arrhythmias of the heart. More particularly, this invention relates to a single lead which can pace within a chamber of the heart.

BACKGROUND OF THE INVENTION

A cardiac pacing system includes a battery-powered pulse generator and one or more leads for delivering pulses to the heart. The pulse generator includes a source of power. Current pulse generators include electronic circuitry for determining the nature of an irregular rhythm, commonly referred to as an arrhythmia, and for timing the delivery of a pulse for a particular purpose. The pulse generator is typically implanted into a subcutaneous pocket made in the wall of the chest. Insulated wires called leads attached to the pulse generator are routed subcutaneously from the pocket to the shoulder or neck where the leads enter a major vein, typically the subclavian vein. The leads are then routed into a chamber or chambers of the heart. The leads are electrically connected to the pulse generators on one end and are electrically connected to the heart on the other end. Electrodes on the leads provide the electrical connection of the lead to the heart. The leads deliver the electrical discharges from the pulse generator to the heart.

The electrodes typically are arranged on a lead body in two ways or categories. A pair of electrodes which form a single electrical circuit (i.e., one electrode is positive and one electrode is negative) positioned within the heart is a bipolar arrangement. The bipolar arrangement of electrodes requires two insulated wires positioned within the lead. The lead with such an arrangement is called a bipolar lead. When one electrode is positioned in or about the heart on a lead and represents one pole and the other electrode representing the other pole is the pulse generator, this arrangement is known as a unipolar arrangement. The unipolar arrangement of electrodes requires one insulated wire positioned within the lead. The lead is called a unipolar lead. Unipolar leads are generally more reliable since there are a lesser number of electrodes. Bipolar leads are advantageous since they tend to reject unwanted local pulses and attenuate far field pulses when sensing. When pacing, the electric field is more localized, helping to prevent interference with other leads. The bipolar lead's sensitivity can be used to prevent interference between two devices implanted in the heart. Pulses from a pacing system need to be ignored so they are not used in making defibrillation decisions, for example. A disadvantage of bipolar leads is that they are larger in diameter than unipolar leads since more conductors are required for a bipolar lead.

There are four main types of pulses which are delivered by a pulse generator. Two of the pulse types are for pacing the heart. First of all, there is a pulse for pacing the heart when it is beating too slowly. The pulses trigger the heart beat. The pulses are delivered at a rate to increase the heart rate to a desired level. The second type of pacing is used on a heart that is beating too fast. This type of pacing is called antitachycardia pacing. In this type of pacing, the pacing pulses are delivered initially at a rate faster than the beating heart. In antitachycardia pacing, the rate of the pulses is slowed until the heart rate is at a desired level. The third and fourth types of pulses are delivered through large surface area electrodes used when the heart is beating too fast or is fibrillating, respectively. The third type is called cardioversion. This is delivery of a relatively low energy shock, typically in the range of 0.5 to 5 joule, to the heart. The fourth type of pulse or signal is a defibrillation pulse which is the delivery of a high energy shock, typically greater than 20 joules, to the heart.

The electrodes attached to the lead and positioned in any chamber of the heart can be used to sense the electrical pulses that trigger the heartbeat. Electrodes detect abnormally slow (bradycardia) or abnormally fast (tachycardia) heartbeats. In response to the sensed bradycardia or tachycardia condition, a pulse generator produces pacing or defibrillation pulses to correct the condition. The same electrode used to sense the condition is also used in the process of delivering a corrective pulse or signal from the pulse generator of the pacemaker.

Some patients require a pacing system having multiple sites in one chamber of the heart for detecting and correcting an abnormal heartbeat. In the past, a common practice for a patient requiring multi-site pacing within one chamber of the heart, would be to provide two separate and different leads attached to the particular chamber of the heart. One lead would be implanted at one site in the chamber. Another lead would be implanted at another site in the chamber. The electrodes on the separate leads would deliver pacing pulses. Typically, the single chamber of the heart receiving multi-site pacing would be the right atrium.

Having two separate leads implanted within the heart is undesirable for many reasons. Among the many reasons are that the implantation procedure for implanting two leads is more complex and also takes a longer time when compared to the complexity and time needed to implant a single lead. In addition, two leads may mechanically interact with one another after implantation which can result in dislodgment of one or both of the leads. In vivo mechanical interaction of the leads may also cause abrasion of the insulative layer along the lead which can result in an electrical failure of one or both of the leads. Another problem is that as more leads are implanted in the heart, the ability to add other leads is reduced. If the patient's condition changes over time the ability to add leads is restricted. Two separate leads also increase the risk of infection and may result in additional health care costs associated with re-implantation and follow-up.

Because of the above problems, there is a need for a single-pass transvenous pacing lead that has electrodes for positioning at multiple sites within a chamber of the heart. A single-pass lead equipped with at least two electrodes would allow for better pacing therapy to a single chamber of the heart. There is still a further need for a single-pass endocardial lead that is easier for a surgeon to implant.

SUMMARY OF THE INVENTION

A single-pass endocardial lead electrode adapted for implantation and for connection to a system for monitoring or stimulating cardiac activity includes a lead body with a circumferential outer surface. The lead includes a distal end having a first pacing electrode or electrode pair. The distal end of the lead body also has a second electrode or electrode pair. The second electrode or electrode pair is positioned away from the first electrode or electrode pair. The first and second electrodes fit within a single chamber of the heart for multi-site pacing or pulse delivery to the single chamber. In a first embodiment, the distal end of the lead body includes a curved portion which facilitates the positioning of the first and second electrode or electrode pair within the single chamber. The first electrode may be a single electrode associated with a unipolar arrangement or may be one of a pair of electrodes associated with a bipolar electrode. The second electrode may be either unipolar or bipolar as well.

In a second embodiment, the lead includes a first leg for the first electrode and a second leg for the second electrode. One of the first or second legs is movable between a withdrawn position and an extended position. When inserting the lead, the withdrawn leg is within the lead body which eases the task of insertion.

In a third embodiment, the two legs may be withdrawn to a position within the lead for easy insertion. In each of the embodiments, the first electrode and second electrode can be passively or actively fixed.

The signals or pacing pulses produced by the pulse generator. The pulse generator can be programmed and the electronics system includes a delay portion so that the timing between a pulse at a first electrode and a pulse at a second electrode.

DESCRIPTION OF THE PREFERRED EMBODIMENT

In the following detailed description of the preferred embodiments, reference is made to the accompanying drawings which form a part hereof, and in which are shown by way of illustration specific embodiments in which the invention may be practiced. It is to be understood that other embodiments may be utilized and structural changes may be made without departing from the scope of the present invention.

Figure 1:
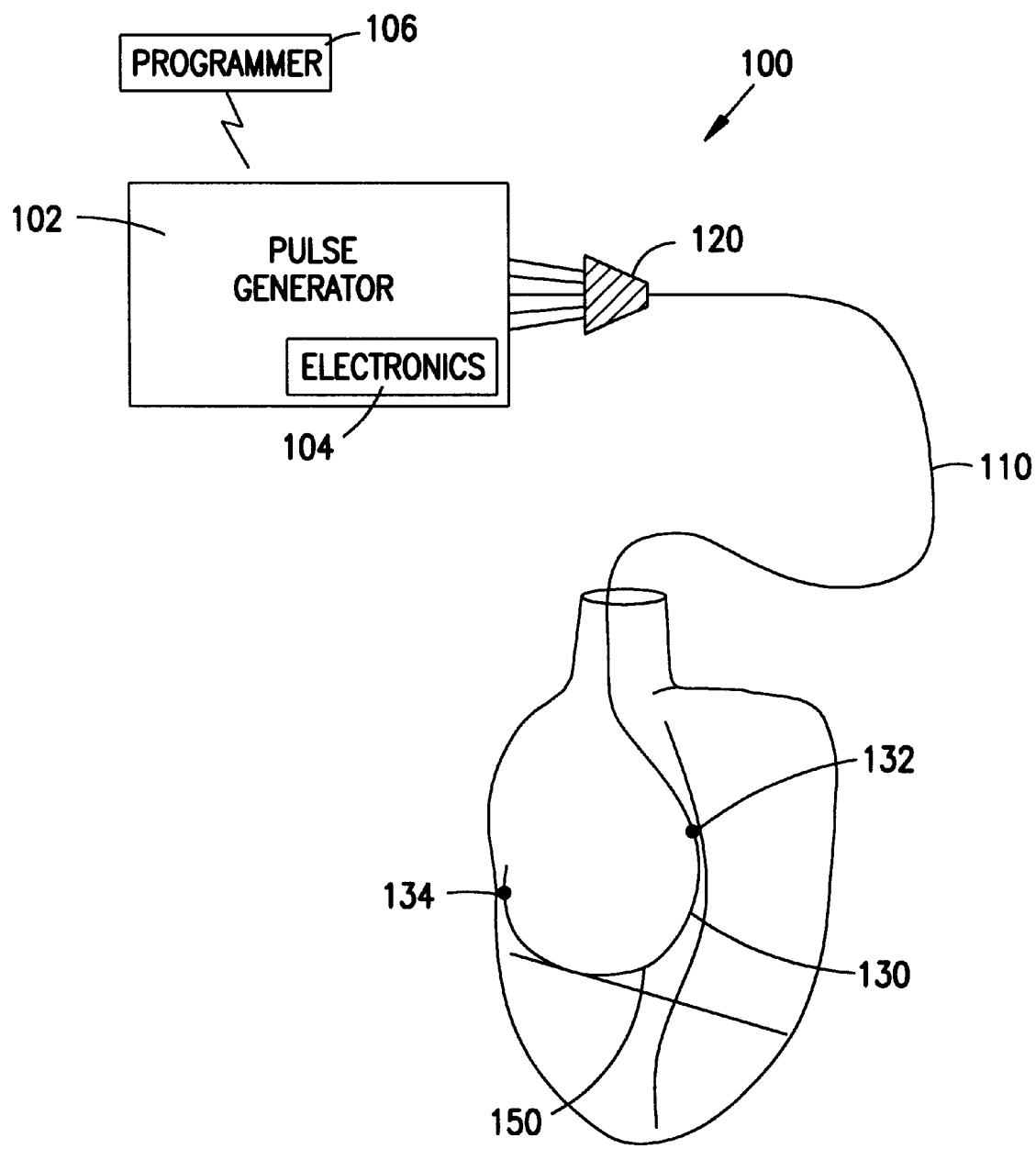
FIG. 1 is a schematic view of the single-pass lead with electrodes for pacing at multiple sites within a single chamber of the heart.

FIG. 1 is a schematic view of a system 100 for delivering electrical pulses or signals to stimulate the heart. The system for delivering pulses 100 includes a pulse generator 102 and a lead 110. The lead 110 includes a connector end or connector terminal 120 and a distal end 130. The distal end 130 of the lead 110 includes at least two electrodes 132 and 134. The electrodes 132 and 134 can be either unipolar or bipolar type electrodes. The electrode 132 would be part of a bipolar set, the second of which is not shown in FIG. 1. Similarly, the electrode 134, if bipolar, would be part of a set. The second electrode associated with electrode 134 is not shown in FIG. 1. The body of the lead 110 is cylindrical in shape. The lead body is comprised of a tubing material formed of a biocompatible polymer suitable for implementation within the human body. Preferably, the tubing is made from a silicon rubber type polymer. The lead body 110 includes several lumens. Lumens carry the electrical conductors from the connector terminal 120 to the electrodes 132 and 134. The electrical conductors carry current and pulses between the pulse generator 102 and the electrodes 132 and 134 located in the distal end 130 of the lead 110. The pulse generator 102 includes a source of power as well as an electronic circuitry portion 104. The pulse generator is a battery-powered device which generates a series of timed electrical discharges or pulses used to initiate depolarization of excitable cardiac tissue. The pulses are delivered to the cardiac tissue and operate as an artificial pulse formation source when used to pace the heart. The pulse generator is generally implanted into a subcutaneous pocket made in the wall of the chest. Alternatively, the pulse generator 102 can be placed in a subcutaneous pocket made in the abdomen. The lead 110 is connected to the pulse generator 102 by the connector terminal 120. The lead travels from the pulse generator and into a major vein and the distal end 130 of the lead is placed inside the heart. The lead is placed underneath the skin and travels to the shoulder and neck where it enters a major vein such as the subclavian vein. The distal end of the lead 110 is placed directly within the endocardium. The lead will typically be either actively or passively affixed to the endocardial wall of a chamber of the heart.

As can be seen in FIG. 1, the distal end 130 of the lead 110 is curved. The curve allows the electrodes 132 and 134 to be positioned in one chamber of the heart. In FIG. 1, the chamber selected for implantation is the right atrium 150. The lead 110 will include a lumen into which a stylet may be placed. The stylet is basically a wire that straightens out the lead while it is being placed within the heart. By removing the stylet, the lead will take on its natural or manufactured shape, which in this case, is a curved distal end 130. The curve within the distal end 130 of the lead 100 has a small enough radius such that it fits within the right atrium 150 of the heart.

The electronics 104 associated with the pulse generator 102 include a delay circuit which allows the pulse delivered to one of the electrodes 132 or 134 to be delayed with respect to the pulse delivered to the other of the electrodes. This delay can be either a delay of zero or it can be a delay that can be programmed to be any desired length of time. The delay portion of the electronics 104 typically will include a clock source. The clock source will produce a clocking pulse that can be used to produce the delay. In other words, if a delay of so many clocking signals equals the appropriate or selected delay, the pulse generator 102 and the electronics 104 will initially deliver a pulse to a first electrode, then the electronics will count the selected number of pulses from a clock signal and then deliver a pulse to the other of the electrodes 132 and 134.

Also shown in FIG. 1 is a programmer 106. The programmer is typically an external-type programmer that can be used to program many of the parameters of the electronics 104 and other parameters of the pulse generator 102. One of the parameters that can be programmed includes the length of delay between the pulse to the electrode 132 and the pulse to the electrode 134. It should be noted that the length of delay can also be set so that it's nonexistent. In other words, if a delay of zero is used, the pulse generator 102 and the electronics associated with the pulse generator 104 will send pacing pulses to the electrode 132 and the electrode 134 at substantially the same time. The programmer can also be an external handheld-type programmer which a user might be able to use. The other type of programmer might be one that a physician would have in his or her office which can be used to program various parameters associated with the pulses produced by the pulse generator. The programmer 106 will typically have a feature which will allow readout of the status of the pulse generator.

It should be noted once again that the electrode 132 may be unipolar or may be bipolar. In addition, the electrode 132 may be actively or passively affixed to the endocardial wall of the heart. When the electrode 132 is bipolar, it is one of a set of electrodes. The electrode 132 is the first electrode in the set and there is another electrode not shown, which is the second electrode of the set. The electrode 134 also may be bipolar or unipolar. When the electrode 134 is bipolar, the electrode is part of a second set of electrodes. In other words, if both of the electrodes 132 and 134 are bipolar, there will be two additional electrodes (i.e., one additional electrode for each of the two sets). Again, either of the electrodes 132 and 134 can be either actively or passively affixed to the endocardial wall of the heart.

Figure 2:
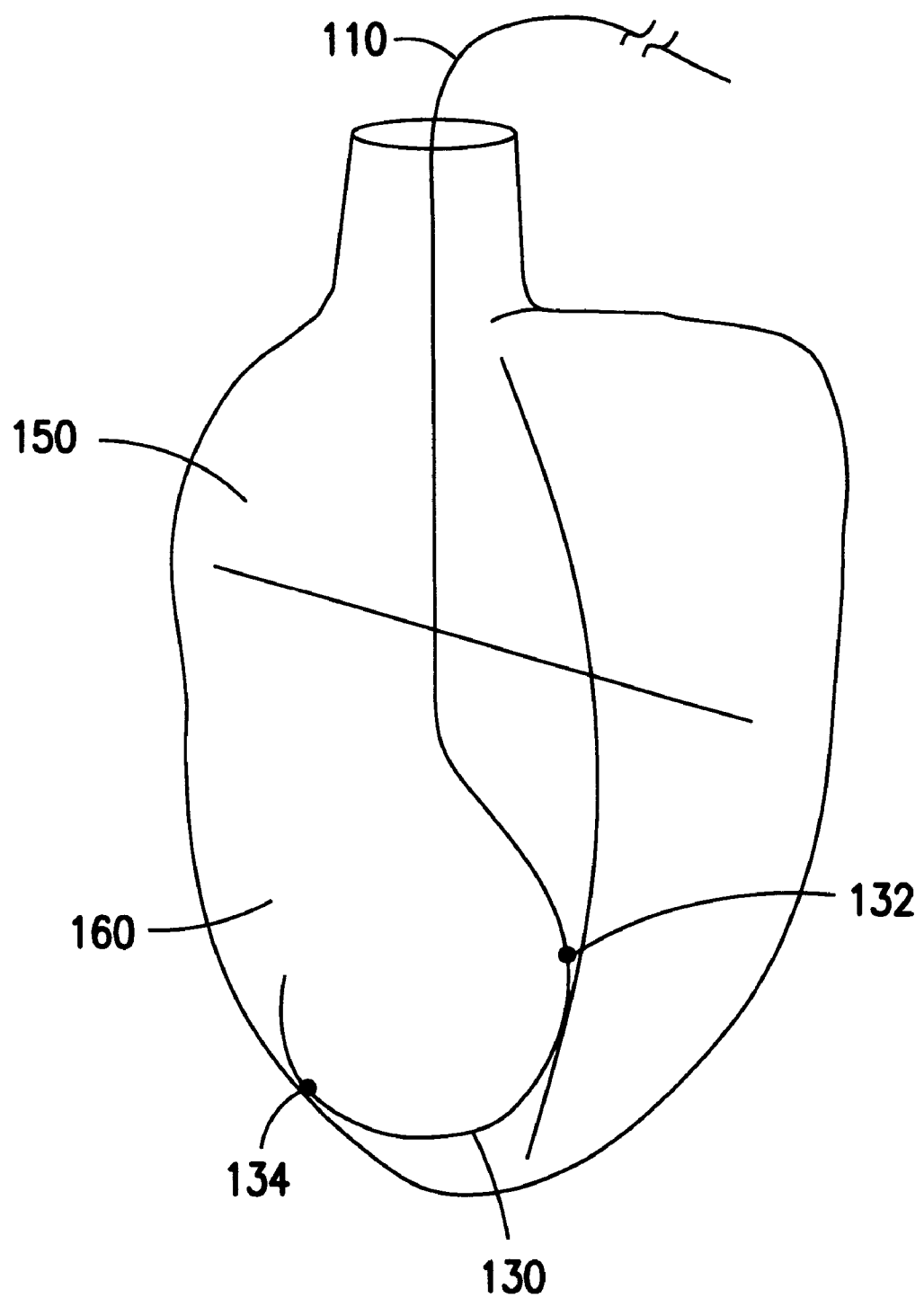
FIG. 2 is a schematic view of the single-pass endocardial lead for electrically stimulating multiple sites within a single chamber of the heart, positioned within the right ventricle of the heart.

FIG. 2 is a schematic of a single-pass endocardial lead for electrically stimulating multiple sites within a single chamber of the heart which is positioned within the right ventricle of the heart. In FIG. 2, the lead 110 is shown as having a distal end 130. The distal end 130 features or includes a first electrode 132 and a second electrode 134. In FIG. 2, the distal end 130 of the lead body 110 is positioned within the right ventricle 160 of the heart. The lead 110 now passes through the right atrium and into the right ventricle 160. Again, as before, the electrodes 132 and 134 may be unipolar or may be bipolar. In the instance when the electrodes 132 are bipolar, there is an additional electrode associated with each of the electrodes 132 and 134. The electrodes 134 and 132 are positioned along the curve in the distal end 130 so that electrical stimulation or pulse generation can be delivered to two sites within a single chamber of the heart, namely, the right ventricle 160. The pulse generator and electronics as well as the connector end or terminal end 120 of the lead 110 and the programmer 106, are all the same in FIG. 1 as in FIG. 2 and, therefore, were not shown here. Again, the electrodes 132 and 134 may be attached to the endocardial wall of the heart via either passive fixation or active fixation. The shape of the curve associated with the distal end may be varied to achieve a selected placement of the electrodes 134 and 132 within the right ventricle of the heart. In addition, the distance between the first electrode 132 and second electrode 134 can also be changed for various applications for multi-site pacing within the right ventricle.

Figure 3:
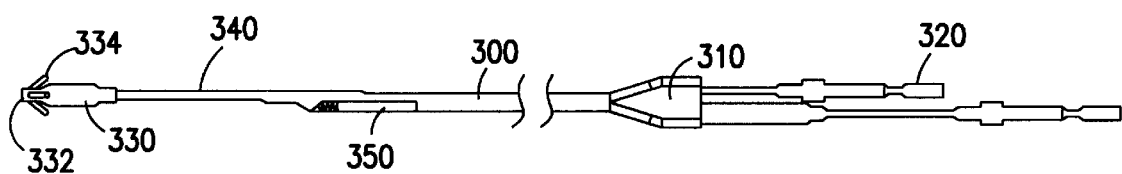
FIG. 3 is a side view of a single-pass endocardial lead for multi-site pacing during insertion with a first atrial leg straight and one atrial leg withdrawn into the lead body.

FIG. 3 is a side view of a single-pass endocardial lead 300 for multi-site pacing within a single chamber of the heart. During insertion, a stylet or wire is placed down a lumen within the lead 300. This makes for a stiffened lead body 300 which can be pushed through the body into the appropriate chamber of the heart. The lead 300 includes a connector end 320 which has a yoke 310. The lead 300 includes a distal end 330. The lead 300 also includes a first leg 340 and a second leg 350. The lead 300 includes a recess which houses the second leg 350. The second leg 350 is maintained within the recess while the lead 300 is being routed through the body, into the major vein or subclavian vein and ultimately into one of the chambers of the heart. The leg 340 and the leg 350 each include an electrode. In FIG. 3, the electrode 332 associated with the first leg 340 is shown. The electrode 332 includes a passive fix element which is a wire mesh screen which allows for the fibers of the heart to grow within the fiber mesh screen over time. Near the electrode 332 are a set of tines 334. The tines 334 also provide for passive attachment of the electrode 332 to the endocardial wall of the specific chamber in the heart to which the first leg 340 of the lead 300 is to be attached.

Figure 4:
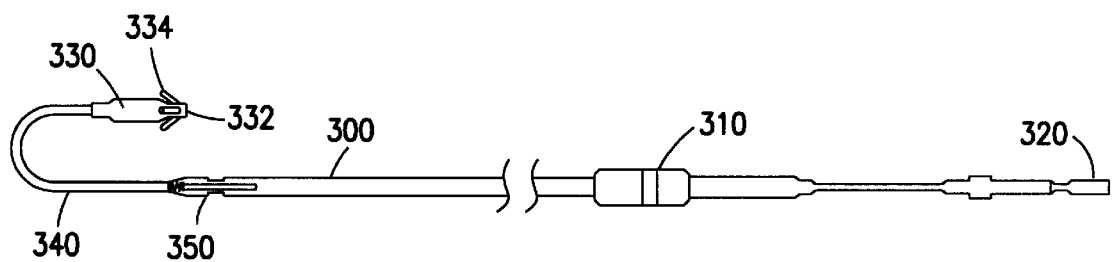
FIG. 4 is a side view of a single-pass endocardial lead for multi-site pacing during insertion with a first atrial leg formed into atrial 'J' after withdrawal of stylet and one atrial leg withdrawn into the lead body.

FIG. 4 is another side view of the lead 300 after the stylet which extends down the body of the lead 300 and into the first leg 340 has been removed. When the stylet is removed, the first leg is allowed to return to its natural state. In this particular case, the first leg 340 of the lead 300 includes a curve therein. The radius of the curve and the length of the leg 340 are or may be varied in order to accomplish placement of the lead 332 at various positions within a particular single chamber of the heart. It should be noted that the second leg 350 is still housed within the recess in the body of the lead 300.

Now turning to FIG. 4, the single-pass endocardial lead 300 for multi-site pacing is shown after the second leg 350 has been removed or pushed out of the recess within the body of the lead 300. The second leg 350 is also J shaped or curved and has an electrode 532 positioned near the free end of the leg 350. The free end of the second leg 350 also includes an active fix element 500 which is used to actively fix the electrode 532 to an endocardial wall of a chamber of the heart. It should be noted that the first leg 340 and the second leg 350 need not be J shaped or curved and that either the first leg or the second leg can both include a passive fix element or they both can include active fix elements. The advantage of this particular configuration is that the passive fix element will not catch on any of the veins or tissue as it is passing through the subclavian vein and into the heart. As this is being done, the active fix portion 500 of the second leg is kept within the recess of the lead body 300 so that the active fix element 500 will not catch on any tissue during insertion. It should also be noted that the radius of the curve and the position and length of the first leg 340 and the second leg 350 can be varied for various applications of multi-site pacing within a single chamber of the heart. It should be noted that for different chambers, different lengths of the legs 350 and 340 might be appropriate, as well as different radii. The configuration shown in FIG. 5 could be placed or positioned within the atrium 150 of the heart. This configuration could be used for simultaneous atrial appendage and Bachman's Bundle pacing.

Figure 5:
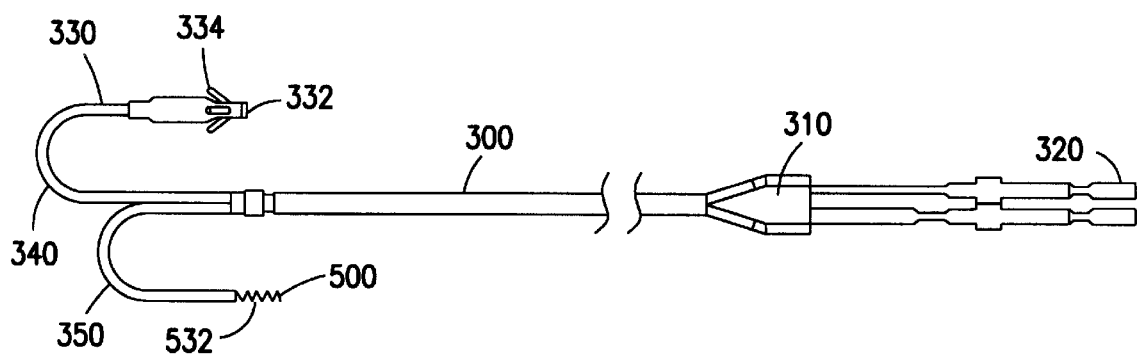
FIG. 5 is a side view of a single-pass endocardial lead for multi-site pacing during insertion with both atrial legs formed into a 'J'.
Figure 6:
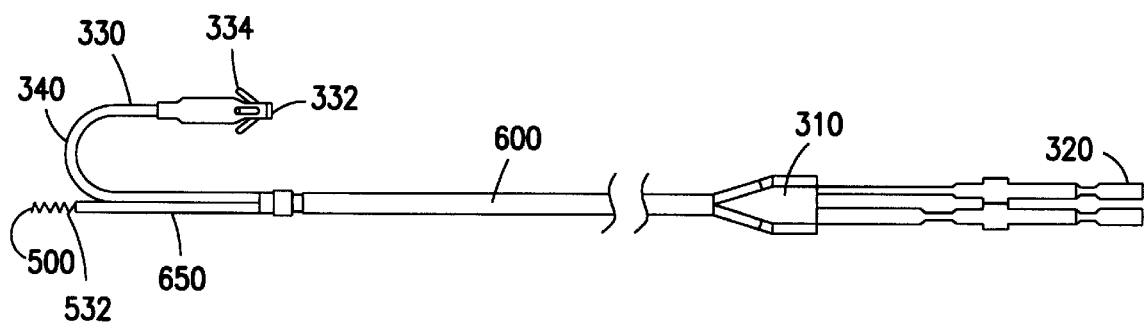
FIG. 6 is a side view of a single-pass endocardial lead for multi-site pacing during insertion with one atrial leg formed into a 'J' (passive) and one leg straight (active).

FIG. 6 shows a variation of a single-pass endocardial lead for multi-site pacing from the ones shown in FIGS. 3–5. The lead 600 shown in FIG. 6 includes many of the same elements of the lead shown in FIGS. 3, 4 and 5. Rather than repeat all the same elements or similar elements between the lead 600 and the lead shown in FIGS. 3, 4 and 5, only the differences will be touched upon or described in the following paragraph. The lead 600 differs from the lead 300 in that the lead 600 includes a second leg 650 which is straight after it has been removed or forced out of the recess in the lead body 600. The second leg 650 includes an electrode 532 as well as an active fix portion 500 for attaching to the endocardial wall of the heart. If this configuration was placed in the atrium, it could be used for simultaneous atrial appendage pacing, and pacing at the entrance of the coronary sinus.

Figure 7:
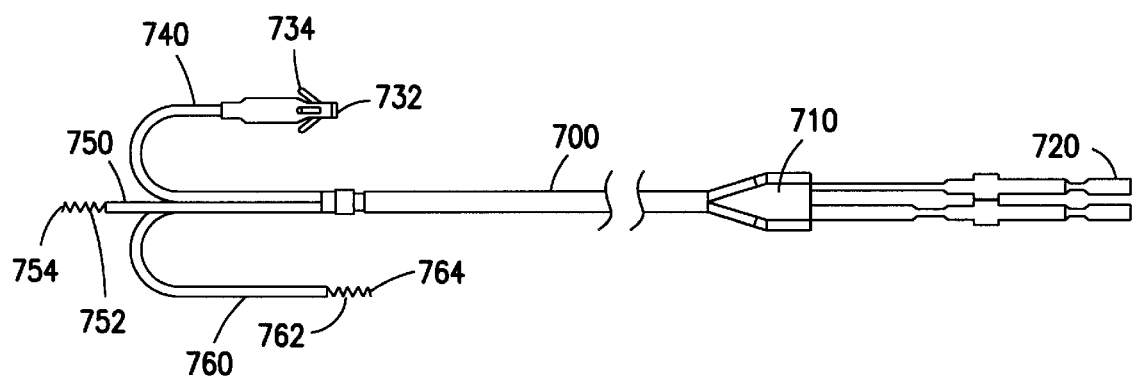
FIG. 7 is a side view of a single-pass endocardial lead for multi-site pacing during insertion with two atrial legs formed into a 'J' (one passive and one active) and one leg straight.

FIG. 7 shows yet another embodiment of a single-pass endocardial lead 700 for multi-site pacing within a single chamber of the heart. The lead 700 includes a connector end 720 and a distal end having a first leg 740, a second leg 750 and a third leg 760. The lead 700 has a recess which is capable of holding a second leg 750 and a third leg 760. The first leg 740 is J shaped or curved and includes an electrode 732 used as part of an active fix element. The first leg 740 also includes a set of tines 734 which enables or allows active fixation of the electrode 732 to an endocardial wall of the heart. The second leg 750 is a straight leg having an electrode 752 and an active fix portion 754. The third leg 760 includes an electrode 762 and an active fix portion 764. During insertion, a stylet is placed into a lumen of the lead 700. The stylet will pass all the way down to and into the first leg 740 of the lead. During insertion, the second leg 750 and the third leg 760 will be housed or in a withdrawn position within either a single recess or a pair of recesses within the lead body 700. With the stylet in place, the lead can be maneuvered and positioned through the major arteries and into the heart. Once it is positioned within the heart, the stylet is removed and a J-shaped natural shape is assumed by the first leg 740. After the lead has been placed within the selected chamber of the heart, the second leg 750 and the third leg 760 can be removed or taken out of the recess in the body of the lead 700. It should be noted that the first, second and third legs may either be curved or J shaped and can also either be attached to the endocardial wall of the heart by active fixation or passive fixation. The position and length of the legs can be varied to produce different multi-site placements of the electrodes within the heart. Each of the electrodes 732, 752 and 762 can be either a bipolar or unipolar configuration. The particular configuration shown in FIG. 7, if placed within the atrium of the heart, can be used for a simultaneous atrial appendage, pacing at the Bachman's Bundle and pacing at the entrance to the coronary sinus.

It is to be understood that the above description is intended to be illustrative, and not restrictive. Many other embodiments will be apparent to those of skill in the art upon reviewing the above description. The scope of the invention should, therefore, be determined with reference to the appended claims, along with the full scope of equivalents to which such claims are entitled.

What is claimed is:

1. A single pass transvenously insertable endocardial lead comprising:
    a lead body;
    a first leg including a first leg lead body and having at least one pacing electrode constructed and arranged for atrial pacing; and
    a second leg including a second leg lead body and having at least one pacing electrode, said first and second leg for positioning within a single chamber of the heart, said chamber being an atrium, the electrode constructed and arranged for atrial pacing;
    wherein the lead is constructed and arranged for transvenous implantation in a patient by subcutaneous placement, advancement to a shoulder and neck of the patient and placement in a major vein and the distal end of the lead is placed directly within an endocardium, the first leg is positioned at a first site within a single chamber of the heart and the second leg is positioned at a second site within the single chamber of the heart for multisite atrial pacing.

2. The lead as recited in claim 1, wherein the lead body has a curved end portion having a curve formed therein, said first pacing electrode and the second pacing electrode located at two positions on the curved end portion, said curved end portion being sized and positioned within the single chamber of the heart so that the first pacing electrode is located at a first position within the single chamber and the second pacing electrode is located at a second position within the single chamber of the heart.

3. The lead as recited in claim 1, wherein the first leg further comprises an active fix element for attaching the first leg to the first site within the single chamber of the heart and the second leg further comprises an active fix element for attaching the second leg to the second site within the single chamber of the heart.

4. The lead as recited in claim 1, wherein the first leg further comprises a passive fix element for attaching the first leg to the first site within the single chamber of the heart and the second leg further comprises a passive fix element for attaching the second leg to the second site within the single chamber of the heart.

5. The lead as recited in claim 1, wherein the second leg is bipolar and further comprises an electrode associated with the second leg.

6. The lead as recited in claim 1, wherein the single chamber of the heart in which the first leg and the second leg are located is the atrium, the lead being constructed and arranged for simultaneous atrial appendage pacing and pacing at the entrance of the coronary sinus.

7. The lead as recited in claim 1 constructed and arranged for simultaneous atrial appendage pacing and Bachman's Bundle pacing.

8. A single pass, transvenously insertable endocardial lead comprising:
    a lead body having a curved end portion having a curve formed therein;
    a first leg including a first leg lead body and having at least one pacing electrode constructed and arranged for atrial pacing; and
    a second leg including a second leg lead body and having at least one pacing electrode, said first and second leg for positioning within a chamber of the heart, said chamber being an atrium, the at least one pacing electrode constructed and arranged for atrial pacing; and
    the first pacing electrode and the second pacing electrode positioned at two positions on the curved end portion of the lead body, the lead constructed and arranged for transvenous implantation in a patient by subcutaneous placement, advancement to a shoulder and neck of the patient and placement in a major vein and placement of the distal end of the lead directly within the endocardium, said curved end portion is positioned within a single chamber of the heart so that the first pacing electrode is located at a first position within the single chamber and the second pacing electrode is located at a second position within the single chamber of the heart for multisite atrial pacing.

9. The lead as recited in claim 8, wherein the first pacing electrode is one of a first set of bipolar electrodes.

10. The lead as recited in claim 9, wherein the second pacing electrode is one of a second set of bipolar electrodes.

11. The lead as recited in claim 8, wherein the second pacing electrode is a unipolar electrode.

12. A system for delivering pulses to the heart, said system comprising:
    an electronics system including a pulse generator which produces pulses to stimulate the heart; and
    a lead adapted for transvenous insertion and endocardial implantation within, on, or about the heart and for connection to the electronics system, said lead comprising:

a lead body;

a first leg having at least one pacing electrode constructed and arranged for atrial pacing; and a second leg having at least one pacing electrode, said first and second leg for positioning within a chamber of the heart, said chamber being an atrium, the at least one electrode constructed and arranged for atrial pacing;

the lead constructed and arranged for transvenous implantation in a patient by subcutaneous placement, advancement to a shoulder and neck of the patient and placement in a major vein and placement of the distal end of the lead directly within the endocardium, whereby the first leg is positioned at a first site within a single chamber of the heart and the second leg is positioned at a second site within the single chamber of the heart for multisite atrial pacing.

13. The system for delivering pulses to the heart as recited in claim 12, wherein the lead body has a curved end portion, said first pacing electrode and the second pacing electrode located at two positions on the curved end portion, said curved end portion being positioned within the single chamber of the heart so that the first pacing electrode is located at a first position within the single chamber and the second pacing electrode is located at a second position with the single chamber of the heart.

14. The system for delivering pulses to the heart as recited in claim 13, wherein the pulse generator produces a first pulse for stimulating the heart at the first position and a second pulse for stimulating the heart at the second position.

15. The system for delivering pulses to the heart as recited in claim 14, wherein the electronics system includes a delay portion for producing a time difference between the first pulse and the second pulse.

16. The system for delivering pulses to the heart as recited in claim 15, wherein the electronics system is programmable, said system further comprising an external programmer for programming the delay portion of the electronics system.

17. A lead comprising:

a main lead body adapted to carry signals to and from a heart when the lead is transvenously inserted and implanted in a single chamber of the heart, the chamber being an atrium, the main lead body having a first recess therein;

a first leg including a first leg lead body, the first leg associated with the main lead body, the first leg including a first atrial electrode;

a second leg including a second leg lead body, the second leg associated with the main lead body, the second leg including a second atrial electrode; and where the first recess receives the entire first leg therein, and the first leg is housed in the first recess during implantation of the lead in an atrium.

18. The lead as recited in claim 17, wherein the second electrode includes a passive fixation element associated therewith.

19. The lead as recited in claim 18, wherein the passive fixation element comprises a mesh screen.

20. The lead as recited in claim 19, wherein the passive fixation element comprises a plurality of tines.

21. The lead as recited in claim 18, wherein the first electrode includes an active fixation element associated therewith.

22. The lead as recited in claim 17, wherein the second leg has a J-shape.

23. The lead as recited in claim 22, wherein the first leg has a J-shape.

24. The lead as recited in claim 16, further comprising a third leg associated with the main lead body, the third leg including a third electrode coupled therewith.

25. The lead as recited in claim 24, wherein the main lead body includes a second recess sized and positioned for entirely receiving the third leg therein.

26. The lead as recited in claim 25, wherein the first leg and the second leg each have a J-shape.

27. The lead as recited in claim 24, wherein the third electrode includes an active fixation element associated therewith.

28. The lead as recited in claim 24 constructed and arranged for simultaneous atrial appendage pacing, Bachman's Bundle pacing, and pacing at the entrance to the coronary sinus.

29. A method for implanting a lead having a lead body, the method comprising:

inserting the lead transvenously until a distal end of the lead is disposed within an atrium, the lead including a first leg having a first lead body and a first electrode and a second leg having a second lead body and a second electrode, the second leg disposed within a recess of the lead body, disposing the first electrode against a wall of the atrium, advancing the second lead body and second leg and second electrode out of the recess of the lead body until the second electrode is disposed against the wall of the atrium.

30. The method as recited in claim 29, further comprising fixating the second electrode against the wall of the atrium with an active fix element.

31. The method as recited in claim 29, wherein the step of advancing the second lead body out of the recess comprises pushing on the second lead body longitudinally.

32. The method as recited in claim 29, wherein the step of advancing the second lead body out of the recess comprises forcing a proximal end of the second lead body toward the distal end of the lead.

33. The method as recited in claim 29, further comprising advancing a third leg having a third lead body and a third electrode out of the recess, where the third leg is advance until the third electrode is disposed against the wall of the atrium.

34. The method as recited in claim 29, further comprising fixating the third electrode against the wall of the atrium with an active fix element.

35. The method as recited in claim 29, further comprising retracting the second leg within the lead body prior to inserting the lead transvenously.

* * * * *